US00PP09637P

United States Patent [19]

Olesen et al.

[11] Patent Number: Plant 9,637

[45] Date of Patent: Sep. 3, 1996

[54] SHRUB ROSE PLANT NAMED 'POULURT'

[75] Inventors: Pernille Olesen; Mogens N. Olesen, both of Fredensborg, Denmark

[73] Assignee: DeVor Nurseries, Inc., Watsonville, Calif.

[21] Appl. No.: 380,102

[22] Filed: Jan. 30, 1995

[51] Int. Cl.[6] ..... A01H 5/00

[52] U.S. Cl. ..... Plt./1

[58] Field of Search ..... Plt./1, 8.2, 24

*Primary Examiner*—Howard J. Locker

*Attorney, Agent, or Firm*—Christie, Parker & Hale, LLP

[57] ABSTRACT

A shrub rose variety producing yellow buds becoming near white to light yellow flowers.

1 Drawing Sheet

SUMMARY OF THE INVENTION

The present invention relates to a new and distinct variety of rose which was originated by crossing as seed and pollen parents two unnamed and undistributed seedlings of our creation. The varietal denomination of this new rose is 'Poulurt'.

Among the novel characteristics possessed by this new variety which distinguish it from its parents and all other varieties of which we are aware are its attractive flowers borne on a healthy and hardy floriferous plant useful in landscaping.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed, such as vegetative cuttings, micropropogation and grafting.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Shrub.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small, about 1 to 1.5 cm long and about 1 cm wide.

(2) *Form.*—Ovoid.

(3) *Color.*—When sepals first divide, bud color is near 15A.

(4) *Sepals.*—About 1.5 cm to about 2.5 cm, longer than bud, sepals spread and then reflex; some sepals are foliaceous. Color: Near 144B at base, darkening to near 144A at tip.

(5) *Peduncle.*—Length: About 2 to about 3 cm. Aspect: Smooth. Strength: Erect, sturdy. Color: Near 144B.

(6) *Bracts.*—Present, leaf-like.

B. Bloom:

(1) *Size.*—Average size when fully expanded — about 4.5 cm.

(2) *Borne.*—Usually in clusters of 5 blooms.

(3) *Form.*—Cupped, loosely imbricated, opens flat to reveal center.

(4) *Petalage.*—Number of petals under normal conditions — about 14 to 18.

(5) *Color (⅓ to ½ open).*— Outer petals — Top surface: near 15A at top ½ of petal with petal fading to 15C at base, occasionally a light blush of near 33A on a petal tip; Undersurface: near 15A at top ½ of petal becoming near 14A at base. Inner petals — Top Surface: near 15A at top ½ of petal becoming near 14A at base; Undersurface: near 15A. Base of petals — (point of attachment): Near 13A. General tonality from a distance: Golden yellow.

(6) *Color (fully open).*—Outer petals — Top surface: near 7D with base near 7C; Undersurface: near 5D with base near 6C. Inner petals — Top surface: near 6D with base near 5C; Undersurface: near 6D with base near 6C. Base of petals — (point of attachment): Near 6A. General tonality from a distance: Lemon yellow.

(7) *Color change.*—As bloom ages: This variety goes from a deep golden yellow to a very uniform lemon yellow then proceeds to light yellow and then to near white. Petal top surface: Lightens slightly. Petal undersurface: Lightens slightly. General tonality at a distance: near white.

C. Petals:

(1) *Texture.*—Thick.

(2) *Appearance.*—Inside and outside matte.

(3) *Form.*—Elliptic with point.

(4) *Arrangement.*—Imbricated but flattens when fully open to reveal center.

(5) *Petaloids.*—Few.

(6) *Fragrance.*–Slight herbal fragrance.

(7) *Lasting quality.*—On plant a few days.

(8) *Persistence.*—Petals drop off cleanly.

REPRODUCTIVE ORGANS

A. Stamens:
(1) *Arrangement.*—Regularly arranged around styles, near 13A.
(2) *Anthers.*—Color near 17A.
(3) *Filaments.*—Color — base and tip near 17A; balance near 33B.
(4) *Pollen.*—Color — color near 17A.

B. Pistils:
(1) *Styles.*—Bunched, uneven.
(2) *Stigmas.*—Color near 151C.

C. Characteristics of hips: Globular to slightly elongated; about 1 cm wide by about 0.9 to about 1.3 cm long; near 177B when mature; seeds do not protrude.

PLANT

A. Form: Compact, free branching.

B. Growth: Very vigorous; height attained about 43 cm to about 55 cm at first season.

C. Foliage: Predominantly compound 7 leaflets.
(1) *Size.*—Small.
(2) *Quantity.*—Abundant.
(3) *Color.*—New foliage — upper side near 137A; underside near 146B; mature foliage — upper side near 147A, underside near 137C.
(4) *Shape.*—Oval with acute tip.
(5) *Texture.*—Upper side semi-leathery; underside smooth.

(6) *Edge.*—Serrated.
(7) *Serration.*—Denticulate.
(8) *Leaf stem.*—Color — medium green.
(9) *Stipules.*—Glandular edges, adnate and parallel.
(10) *Rachis.*—Very small prickles on underside.
(11) *Petioles.*—Top near 147B, underside near 146C.
(12) *Auricle.*—Thin, tipped with glands.
(13) *Resistance to disease.*—Very resistant to blackspot, mildew and rust.

D. Wood:
(1) *New wood.*—Color near 173C, bark smooth.
(2) *Old wood.*—Color from near 146A to near 146B, bark smooth.

E. Flower stem: About 12 cm to about 35 cm from last cut.

F. Thorns:
*Quantity.*—On main stalk, average laterals from stalk, some.
*Form.*—Thin.
*Length.*—Medium.
*Color.*—Near 162B at base with near 183C at tip.
*Position.*—Irregular.
*Prickles.*—None on stems.

G. Winter hardiness: Winter hardy in Denmark and in Watsonville, Calif.

I claim:

1. A new and distinct variety of rose plant, substantially as shown and described.

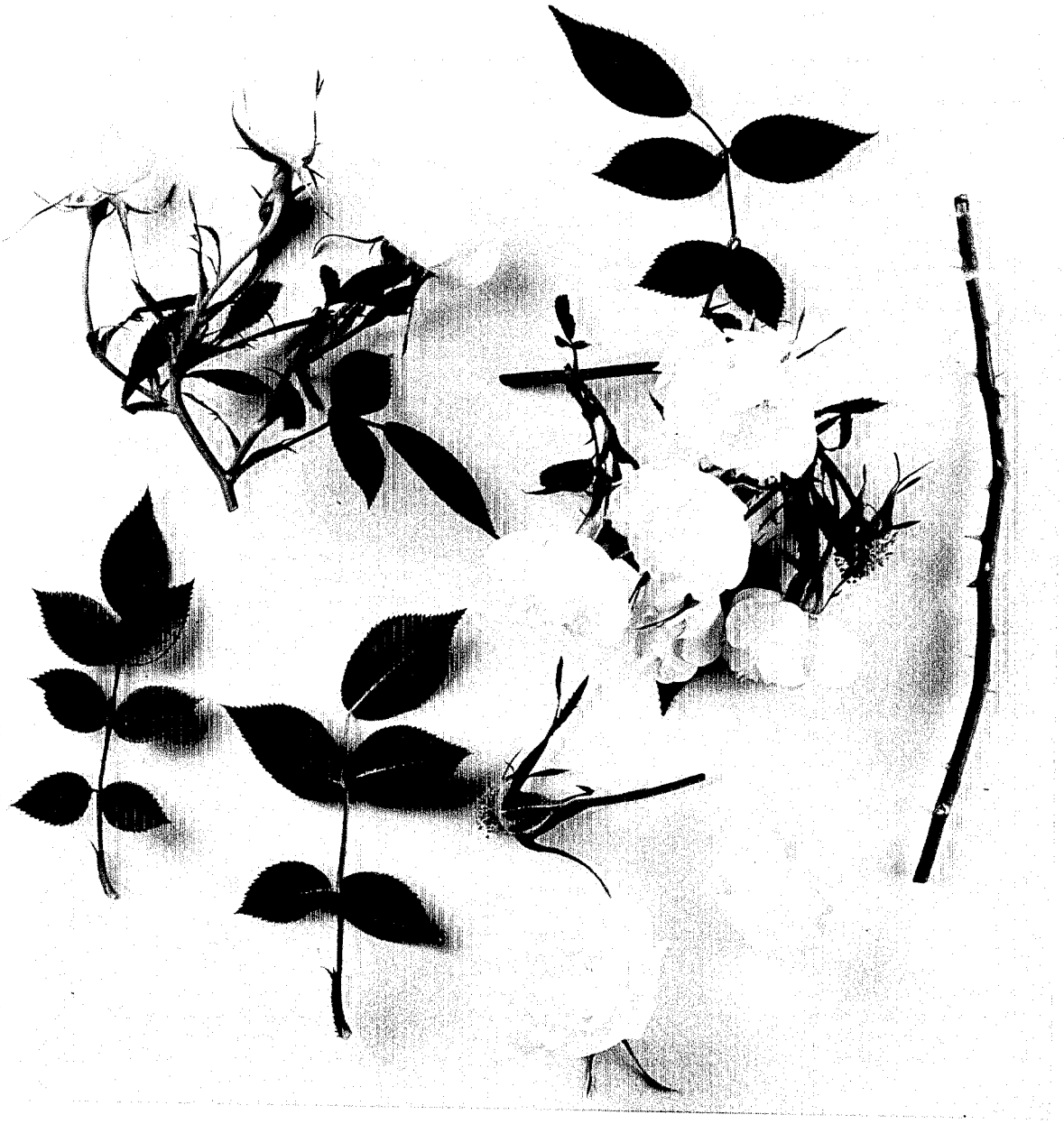

* * * * *